Figure 1:
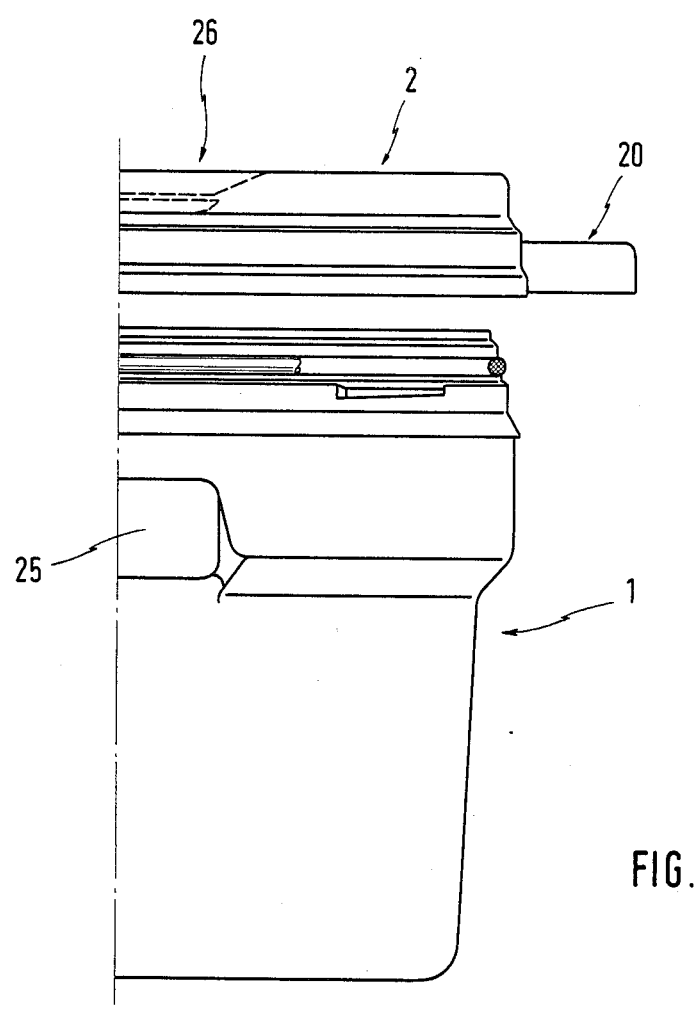

United States Patent [19]

Otto et al.

[11] Patent Number: 4,877,150

[45] Date of Patent: Oct. 31, 1989

[54] DISPOSABLE CONTAINER

[76] Inventors: Werner Otto, Forstweg 2, D-5910 Kreuztal; Ulrich Beese, Brunnenstrass 6, D-5963 Wenden-Hünsborg; Martin Schmidt, Am Zollstock 11, D-3565 Breidenbach-Achenbach, all of Fed. Rep. of Germany

[21] Appl. No.: 138,444

[22] Filed: Dec. 28, 1987

[30] Foreign Application Priority Data

Jan. 12, 1987 [DE] Fed. Rep. of Germany ....... 3700683

[51] Int. Cl.[4] ............................................. B65D 43/14
[52] U.S. Cl. .................................... 220/304; 206/366; 206/807; 220/1 T; 220/308
[58] Field of Search ................ 206/366, 807; 220/1 T, 220/306, 307, 308, 324–326, 288, 304

[56] References Cited

U.S. PATENT DOCUMENTS

| 4,034,889 | 7/1977 | Hammes et al. | 220/324 |
| 4,371,092 | 2/1983 | Teague | 220/324 |
| 4,488,643 | 12/1984 | Pepper | 206/366 |
| 4,520,926 | 6/1985 | Nelson | 206/366 |
| 4,552,280 | 11/1985 | Owen et al. | 220/1 T |
| 4,609,125 | 9/1986 | Willingham | 220/324 |
| 4,657,139 | 4/1987 | Hanifl | 206/366 |
| 4,715,498 | 12/1987 | Hanifl | 220/1 T |

FOREIGN PATENT DOCUMENTS

| 2551820 | 6/1977 | Fed. Rep. of Germany | 220/306 |
| 0056035 | 6/1934 | Norway | 220/306 |

Primary Examiner—Jimmy G. Foster
Attorney, Agent, or Firm—Paul L. Sjoquist

[57] ABSTRACT

The disposable container comprising a lid can be firstly provisionally and secondly finally sealed by means of two different fasteners or closure means, and the final closure means cannot be opened again without destruction of said means. The provisional closure means (14) suitable for repeated use in formed such that on closure a sealing is provided by compression of a seal provided on the container outer side between the container border and the lid and consisting of a sealing ring and an encircling counter face (11).

19 Claims, 1 Drawing Sheet

DISPOSABLE CONTAINER

The invention relates to a disposable container, in particular for hospital waste, comprising a filling opening closable by means of a lid, the lid overlapping the encircling border of the filling opening by means of a lid border directed axially of the filling opening, and a closure means not releasable without destruction, in which an engagement edge disposed on the cover border engages over a retaining projection on the container.

Since such waste containers during use are located in operating theatres or in wards they must be at least in a hygienically satisfactory condition, i.e. to a certain extent free from bacteria. Sterilizing containers used several times is expensive and relatively complicated. For this reason one-way disposable containers are used which after filling are firmly sealed and are disposed of by incineration.

DE-OS 3,436,399 discloses a disposable container for hospital waste in which the lid with its encircling downwardly directed groove is placed on the upper free border edge of the container. At the opposing groove walls projections stand out between which the wedge-shaped border is pushed. At the same time the lid is sealed by an integrally formed sealing lip which comes to bear on an inclined face of the container inner wall.

The closure means or fastener which cannot be released without destruction comprises a rib which extends inclined downwardly and is formed at the outer periphery of the border region and behind the free end of which a corresponding detent or engagement edge of the lid engages.

This container has considerable disadvantages. Firstly, the fitted lid, which merely clamps the wedge-shaped free border of the container opening, does not ensure that the container remains sealed should it fall over during use. There is a danger that the clamping action between the inwardly directed groove with the projections integrally formed thereon and the wedge-shaped border edge of the filling opening is not sufficient to withstand the shock caused by falling over. Also, the sealing lip formed on the container inner wall is a disadvantage because it can easily happen that when the container is full waste material projects to such an extent that it comes to lie unnoticed between this sealing lip and the container inner wall. This endangers a reliable sealing and it is then possible that germs can escape.

The invention is based on the problem of improving a container of the aforementioned type in such a manner that said container on temporary closure always provides a reliable closing action and the seal of which avoids any danger of clamping or wedging in waste both in the temporary and in the final sealing.

The problem is solved according to the invention in that the sealing ring at the outer periphery of the container in the border region is accommodated beneath the filling opening in an encircling groove and an encircling counter face formed on an associated portion of the lid border is adapted to be pressed against the sealing ring and that the lid is additionally formed with a closure means which is suitable for repeated use and which with the closure simultaneously ensures a sealing by pressing the counter face against the sealing ring.

It is ensured with the aforementioned features that the wedging of waste material between the cooperating sealing elements of the lid and of the container is not possible because the person using the container notices waste material hanging over the filling opening and can push this waste back into the container. The formation of the repeatedly usable closure means or fastener in the form of a threaded fastener or closure means provides high security against unintentional opening should the container be knocked over; the bearing of the support face against the sealing ring in the sealing groove on provisional closure seals the container in an odour-proof manner and ensures that no liquid can run out of a container which has been knocked over because the seal provides an adequate sealing effect on fastening by means of the turn fastener or closure means. For the final sealing the lid is locked after being screwed on by firm pressing on. The pressure to be applied to the lid when this is done is less than in the prior art because the screwing on has already applied a partial pressure. Thus, the final sealing is facilitated by the features according to the invention.

Advantageously, the groove can be arranged laterally at the outer periphery of the container with radially outwardly directed opening, the lower groove wall projecting radially beyond the upper groove wall. It is expedient to form the counter face substantially as inclined face.

Advantageously, the radially inner groove wall of the inner groove extends substantially up to the height of the inclined face or of the groove for the sealing ring. Said groove wall comes to bear on the groove wall projecting convexly inwardly into the container for the sealing ring and thus forms firstly an abutment for the pressing operation on sealing and secondly an independent additional seal.

Advantageous further embodiments are set forth in the further subsidiary claims.

Figure 2:
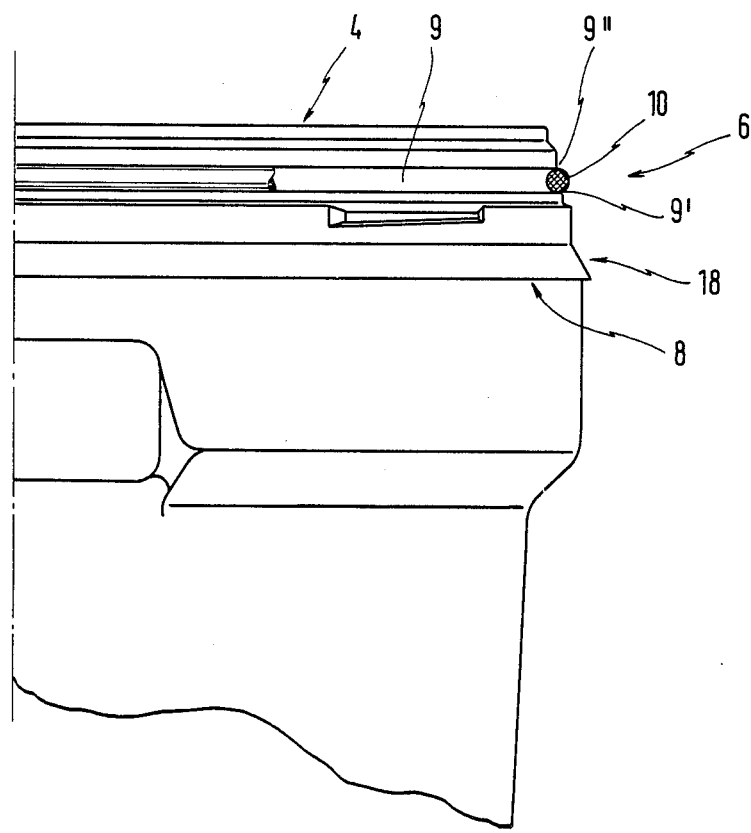
Figure 3:
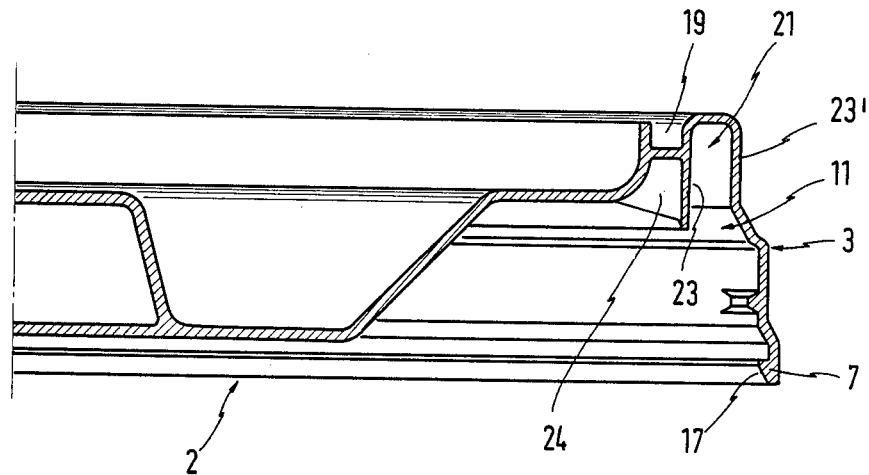
Figure 4:
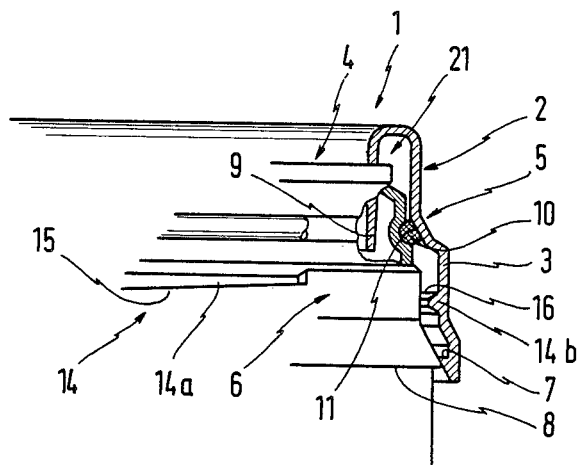
Figure 5A:
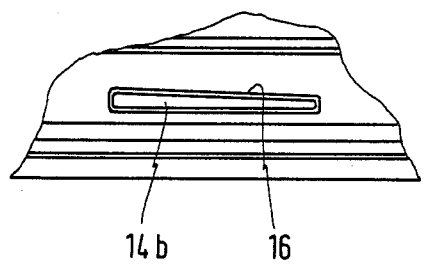
Figure 5B:
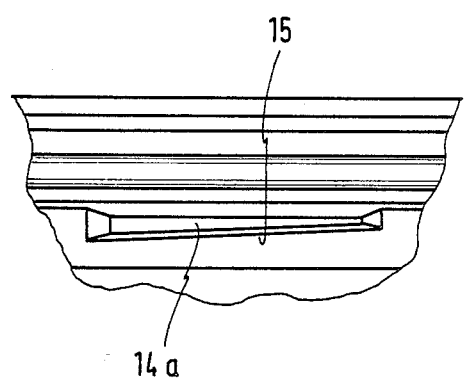
Figure 6:
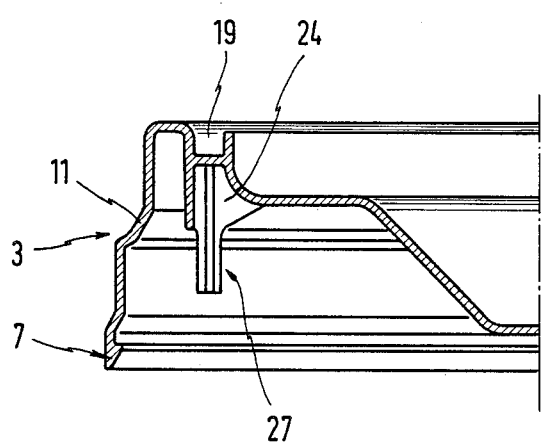

Hereinafter the invention will be explained in detail with reference to examples of embodiment illustrated in the drawings, wherein:

FIG. 1 is a partial view in side elevation of a disposable container according to the invention with lid, FIG. 2 is an enlarged partial view in side elevation of the edge region of the filling opening, FIG. 3 is an axial section through part of the lid, FIG. 4 is a partial view of the container with the lid fitted, FIGS. 5A show details of the ramp-like projections of the and 5B turn fastener or closure means, FIG. 6 is a further axial section through the lid.

In FIG. 1 a disposable container 1 with a lid 2 is illustrated. The lid comprises a radially projecting hand grip 20 and another hand grip 26 on its depressed upper side. On the container diametrically opposite grips 25 are formed. The container shown in FIG. 1 has a volume of about 30 litres. The invention is however also applicable to containers with a greater volume capacity, for example 60 litres.

In the illustration of FIG. 2 the reference numeral 4 denotes the filling opening. In the border region 6 beneath the filling opening 4 an encircling groove 9 is integrally formed. The groove is formed such that the container-side portion 9' projects radially further outwardly than the portion 9" directed upwardly towards the filling opening. This specific configuration gives an additional support for the sealing ring 10 which is inserted into the groove. The sealing ring cooperates with a counter face 11 which is formed on a corresponding point of the lid 2. This counter face 11 is formed as inclined face in the present example or embodiment. On closing the lid said counter face comes to bear against the sealing ring 10 and with a force component directed downwardly substantially inclined to the axis of the container presses the sealing ring 10 into the sealing groove 9 (cf. FIG. 4).

Beneath the seal denoted generally by the reference numeral 5 in FIG. 4 a turn fastener or closure means 14 is formed. The turn fastener or closure means 14 consists firstly of ramp-like projections 14a disposed on the container and having a downwardly directed ramp face 15 and secondly of complementary projections 14b with upwardly directed ramp faces 16 formed at a corresponding point on the lid. When the lid is turned these projections come into mutual engagement in the manner of thread flanks and generate an axially directed force which leads to compression of the seal 5. The slope of the ramp faces 15, 16 is chosen such that an overturning of the fastener or closure means is not possible. To obviate this danger a stop face (not shown) can also be provided on the corresponding end of the ramp face of a projection 16 or projection 15.

At the free end of the lid border 3 directed axially with respect to the container a detent edge 7 is formed in the manner of a hook and has an inclined slide face 17. Said engagement edge 7 on final sealing of the container engages behind a retaining projection 8 which is integrally formed directly on the outer periphery of the side wall of the container, application of a greater force being necessary to enable the detent edge 7 to be brought into the closure position by jumping over the retaining projection 8. This force application serves firstly to compress the seal and secondly for resilient widening of the free border of the lid 3 which returns to its original position when the detent edge 7 has jumped over the retaining projection 8 on the lid. The jumping over is facilitated by slide face 18 which when the lid is pressed onto the container cooperates with the slide face 17 on the detent projection.

This closure means cannot be released again without destructive application of force. A further difficulty can be established by forming the slide face 17 not as an inclined face but as a face formed parallel to the wall beneath the retaining projection 8 so that an almost hermetic and gapfree locking is achieved (not shown).

Formed at the lower side of the lid is an encircling groove 21 into which the free edge 22 of the filling opening 4 can enter. The radially inner groove wall 23 of the inner groove 21 is drawn downwardly to such an amount that it extends up to the height of the opposite inclined face 11, the latter adjoining the radially outward groove wall 23' downwardly. The inner groove wall 23 is supported by means of support ribs 24, said support ribs 24 simultaneously ensuring stabilization of an encircling stack groove 19 on the lid surface.

The engagement of the radially inner groove wall 23 on the radially inwardly projecting wall of the container 1 provides firstly a support for the seal 5 and secondly an independent further sealing. FIG. 6 shows a further detail of the lid. Axial projections 27 serving to centre the lid on the filling opening 4 are provided at least on four support ribs 24 distributed at regular intervals over the periphery.

In a modified embodiment not shown the inclined face may be formed as curved concave face adapted to a greater or lesser extent to the shape of the sealing ring.

We claim:

1. A disposable container and lid, having both a releasable seal and a non-releasable seal, comprising (a) a container having a filling opening at one end and a sealing ring about its outer periphery proximate said one end, said container further having an outer surface extending away from said one end; a container locking projection extending from said outer surface; and an outwardly increasing ramp face extending from said outer surface, said ramp face terminating in a retaining projection; and (b) a lid sized for closure of said filling opening, said lid having a downwardly projecting inner edge surface, said inner edge surface having an inner encircling counter face engageable against said sealing ring; said inner edge surface also having a lid locking projection extending inwardly from said surface and engageable in releasable locking engagement against said container locking projection; said inner edge surface terminating in an inwardly directed detent engageable in non-releasing locking engagement against said retaining projection, whereby said sealing ring is partially compressed when said lid locking projection is in locking engagement with said container locking projection, and said sealing ring is further partially compressed when said detent is in locking engagement against said retaining projection.

2. The apparatus of claim 1, further comprising a groove about the container outer periphery proximate said one end, wherein said sealing ring is seated in said groove.

3. The apparatus of claim 2, wherein said groove further comprises an upper groove wall and a lower groove wall, and said lower groove wall extends further outwardly than said upper groove wall.

4. The apparatus of claim 3, wherein said lid inner encircling counter face further comprises an inclined plane along said inner edge surface.

5. The apparatus of claim 1, wherein said lid further comprises a downwardly facing inner peripheral groove sized to accept said container filling opening end, including an inner groove wall engageable against the interior surface of said container proximate said filling opening to form a further seal.

6. The apparatus of claim 5, wherein said lid further comprises an upwardly facing stack groove, and supporting ribs extending between said stack groove and said inner peripheral groove.

7. The apparatus of claim 1, further comprising a hand grip affixed to said lid.

8. The apparatus of claim 1, further comprising a plurality of downwardly extending projections on said lid, positioned to insert into said container filling opening and thereby guide said lid into closure position over said filling opening.

9. The apparatus of claim 1, wherein said sealing ring is disposed between said container locking projection and said filling opening.

10. A disposable container and lid, having both a releasable seal and a non-releasable seal, comprising a container having a filling opening at one end and a sealing ring about the outer periphery of said container proximate said one end; a lid sized for fitting over said container one end in closure of said filling opening; turn fastening means for releasably locking said lid to said container with said lid partially compressing said sealing ring; and snap fastening means for non-releasably locking said lid to said container with said lid partially compressing said sealing ring.

11. The apparatus of claim 10, further comprising a peripheral groove about said container, with said sealing ring being seated in said groove.

12. The apparatus of claim 11, wherein said lid further comprises an inner counter face engageable against said sealing ring.

13. The apparatus of claim 10, wherein said snap fastening means further comprises an outwardly projecting ridge about said container and an inwardly projecting ridge about said lid.

14. The apparatus of claim 10, wherein said lid further comprises a downwardly facing groove sized to accept said container one end, said groove having an inner groove wall engageable against an inner wall of said container filling opening.

15. The apparatus of claim 14, wherein said lid further comprises an upwardly facing stack groove.

16. The apparatus of claim 10, wherein said lid further comprises a hand grip.

17. The apparatus of claim 10, wherein said lid further comprises a plurality of downward projections spaced for fitting into said container filling opening and guiding said lid into closure position.

18. The apparatus of claim 13, wherein said inwardly projecting ridge about said lid is formed along an edge of said lid.

19. The apparatus of claim 10, wherein the sealing ring is positioned between the filling opening and the turn fastening means.

* * * * *